United States Patent [19]

Reynolds

[11] Plant 4,116

[45] Sept. 27, 1977

[54] ALMOND TREE

[76] Inventor: Samuel M. Reynolds, 3804 Washington Blvd., Livingston, Calif. 95334

[21] Appl. No.: 740,474

[22] Filed: Nov. 10, 1976

[51] Int. Cl.[2] ..... A01H 5/03

[52] U.S. Cl. ..... Plt./30

[58] Field of Search ..... Plt./30

*Primary Examiner*—Robert E. Bagwill

*Attorney, Agent, or Firm*—Roger B. Webster

[57] ABSTRACT

An almond tree which is of medium size, dense, vigorous, spreading, abundantly foliated with medium size, acuminate, acutely pointed leaves having a crenate, finely serrate margin, and alternate, globose glands on the petiole, blooms heavily with white flowers, and regularly heavily bears large, well-distributed nuts having a medium size kernel.

1 Drawing Figure

ORIGIN OF THE VARIETY

The present variety of almond tree was discovered by me growing, as a chance seedling, on my ranch located near Livingston, Merced County, Calif. Under continuing observation, I recognized that the variety possessed certain novel characteristics and, therefore, undertook asexual reproduction of the variety.

ASEXUAL REPRODUCTION OF THE VARIETY

Subsequent to my discovery of the present variety, and recognition of its novel characteristics, I asexually reproduced the variety—on my ranch located as aforesaid—by budding. In maturity, the asexual reproductions ran true to the original tree in all discernible respects.

SUMMARY OF THE VARIETY

The herein claimed, new and distinct variety of almond tree is of medium size, dense, vigorous, spreading, abundantly foliated with medium size, acuminate, acutely pointed leaves having a crenate, finely serrate margin, and alternate, globose glands on the petiole, blooms heavily with white flowers, and regularly heavily bears large, well-distributed nuts having a medium size kernel.

The herein claimed, new and distinct variety of almond tree is further characterized, in comparison to the Nonpareil (unpatented), in the following respects:

1. While similar in vigor, the present variety of almond tree has sturdier branches, somewhat denser growth, and—although essentially spreading—is more upright in tree structure.
2. The blooming period is about one week later, reducing the chance of frost damage.
3. There is less pre-harvest nut drop, yet easier harvest detachment of the nuts from the tree.
4. The harvest period is about a week later while having a number of the same desirable qualities, such as high crack-out, and attractive kernels with excellent flavor; the crack-out being somewhat greater than the Nonpareil, and the kernels being more plump.

BRIEF DESCRIPTION OF THE DRAWING

The drawing is an illustration, by photographic reproduction in color, of a twig with leaves and nuts and, detached, nuts in hull, nuts out of hull, and cracked-out kernels.

DESCRIPTION OF THE VARIETY

The botanical details of this new and distinct variety of almond tree—with color definitions (except those in common color terms) referenced to Maerz and Paul Dictionary of Color—are as follows:

TREE

Density: Dense.
Size: Medium.
Vigor: Vigorous.

TRUNK

Form: Stocky.
Texture: Medium.

BRANCHES

Form: Stocky.
Texture: Smooth.
Lenticels:
*Number.*—Medium.
*Size:*—Medium.
Branching Habit: Spreading, but more upright than Nonpareil.
Color:
*New Wood.*—Reddish brown.
*Mature Wood.*—Brown; Semi-glossy.

FOLIAGE

Quantity: Abundant.

LEAVES

Size: Medium.
*Average length (including petiole).*—10.1 cm.
*Average width.*—2.5 cm.
Shape: Acuminate; Acutely pointed.
Thickness: Thin.
Texture: Smooth.
Margin: Crenate; Finely serrate.
Petiole: Long; Medium thickness.
Glands: Number — 1 to 3. Alternate; Small; Globose; Green; Positioned on petiole at base of blade.
Stipules: Wanting.
Color:
*Top Side.*—Glossy dark green (23-L-9).
*Under Side.*—Dull lighter green (22-J-7).

BLOOM

Amount of bloom: Heavy.

Color: White.
Blooming period: February 25th - March 6th. Late, as compared to Nonpareil and Merced (U.S. Plant Pat. No. 1,730).

CROP

Bearing: Regular bearer.
Productivity: Heavy.
Distribution of nuts on tree: Well distributed.
Ripening (Harvest) period: September 20th - September 30th. Medium, as compared to Merced and Carmel (U.S. Plant Pat. No. 2,641). Late, as compared to Nonpareil.
Tenacity: Hangs well on tree; Easy to harvest; Easy to hull.

HULL

Outer Surface: Rough.
Pits: Pitted.
Form: Regular.
Thickness: Thin.
Flesh: Tough.
Suture: Ridged.
Color: Light green (20-J-5) with silvery pubescence.
Dehiscence: Opens freely.
Splitting: Mostly along suture; sometimes down back; freely at base.

NUT

Size: Large.
*Average length.*—3.58 cm.
*Average width.*—2.14 cm.
*Average thickness.*—1.2 cm.
*Average weight.*—1.8 gr.
Form:
*Length/width.*—Elongated — ovate.
*Width/thickness.*—Medium.
Shell: Paper.
*Outer shell.*—Largely missing. Adherent to hull.
*Inner shell.*—Hard. Poorly sealed.
Color: Medium light tan (12-L-7).
Pits: Large; Numerous; Deep; Round.
Base: Ventrally oblique.
Stem scar: Large. Obtuse.
Apex: Acute; Sharp; Prolonged at tip.
Wing: Broad; Thin; Tapered toward apex.
Inner surface: Medium.
Percentage of kernel to nut: 69.2%.

KERNEL

Size: Medium.
*Average length.*—25.45 mm.
*Average width.*—12.1 mm.
*Average thickness.*—8.4 mm.
*Average weight.*—1.3 gr.
Form:
*Length/width.*—Elongated — ovate.
*Width/thickness.*—Medium.
Base: Ventrally oblique.
Stem scar: Large.
Apex: Acute; Tip recurved.
Plumpness: Furrowed.
Pellicle: Thin.
Pubescence: Medium; Veined.
Color: Medium light brown (13-K-8) with darker striations.
Number of doubles: Medium.
Defective kernels: Few.
Flavor: Dry; Sweet.
Quality: Very good.

SUSCEPTIBILITY OR RESISTANCE TO INSECTS AND DISEASES

Apparent substantial resistance to fungus and spider mites.

The almond tree and its nut herein described may vary in slight detail due to climatic and soil conditions under which the variety may be grown; the present description being of the variety as grown in the Central Valley of California.

I claim:

1. A new and distinct variety of almond tree, substantially as illustrated and described, which is of medium size, dense, vigorous, spreading, abundantly foliated with medium size, acuminate, acutely pointed leaves having a crenate, finely serrate margin, and alternate, globose glands on the petiole, blooms heavily with white flowers, and regularly heavily bears large, well-distributed nuts having a medium size kernel; the variety being particularly characterized, in comparison to the Nonpareil, by sturdier branches, denser growth, more upright tree structure, a blooming period about one week later, less pre-harvest nut drop and easier harvest detachment, a harvest period about a week later, higher crack-out of kernels, and kernels which are more plump.

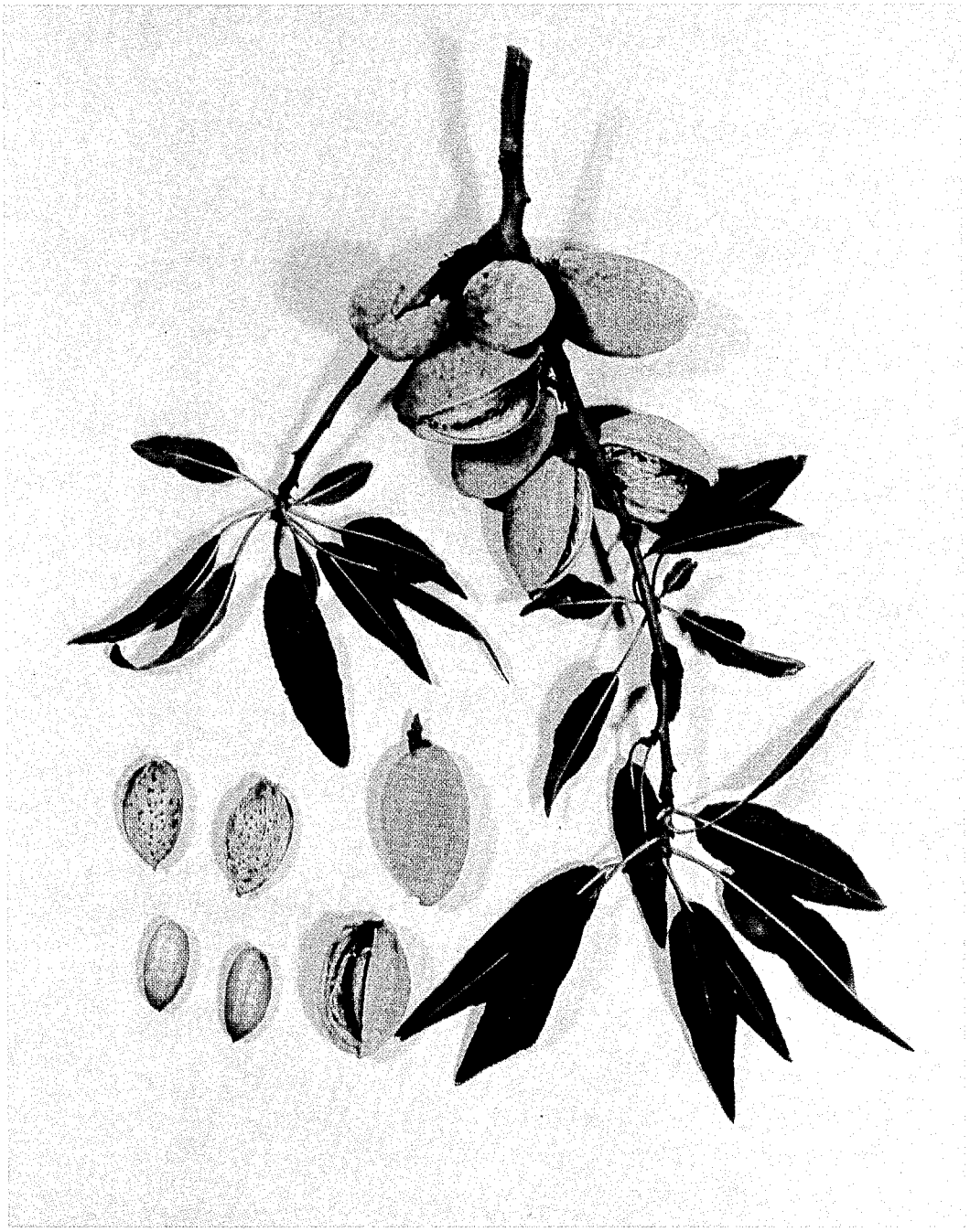

* * * * *